(12) United States Patent
Tatarko

(10) Patent No.: US 7,988,856 B2
(45) Date of Patent: Aug. 2, 2011

(54) WASTE WATER TREATMENT

(75) Inventor: Matthew Tatarko, Lakeside, TX (US)

(73) Assignee: Novozymes Biologicals, Inc., Salem, VA (US)

( * ) Notice: Subject to any disclaimer, the term of this patent is extended or adjusted under 35 U.S.C. 154(b) by 0 days.

(21) Appl. No.: 12/770,119

(22) Filed: Apr. 29, 2010

(65) Prior Publication Data

US 2010/0213122 A1 Aug. 26, 2010

Related U.S. Application Data

(63) Continuation of application No. 12/101,296, filed on Apr. 11, 2008, now Pat. No. 7,731,851.

(60) Provisional application No. 60/911,308, filed on Apr. 12, 2007.

(51) Int. Cl.
*C02F 3/00* (2006.01)

(52) U.S. Cl. ......... 210/605; 210/620; 210/630; 210/611

(58) Field of Classification Search .................. 210/611, 210/620, 630, 605
See application file for complete search history.

(56) References Cited

U.S. PATENT DOCUMENTS

| 4,225,381 | A | 9/1980 | Ishikawa |
| 5,037,551 | A | 8/1991 | Barkley et al. |
| 7,160,458 | B2 | 1/2007 | Pezzetta |
| 7,270,751 | B2 | 9/2007 | Fleury |
| 2005/0115892 | A1 | 6/2005 | Fleury |
| 2006/0108283 | A1 | 5/2006 | Johnson |
| 2006/0194303 | A1 | 8/2006 | DeWitt et al. |
| 2007/0060477 | A1 * | 3/2007 | Pedersen et al. .............. 504/100 |

FOREIGN PATENT DOCUMENTS

| DE | 10 2004 020 837 | 12/2005 |
| EP | 1 352 953 | 10/2003 |
| EP | 1 679 287 | 7/2006 |
| WO | WO 03/076351 | 9/2003 |
| WO | WO 2006/070391 | 7/2006 |
| WO | WO 2006/072629 | 7/2006 |

* cited by examiner

*Primary Examiner* — Chester T Barry
(74) *Attorney, Agent, or Firm* — Thomas C. Sova, IV

(57) ABSTRACT

The present invention relates to wastewater treatment in general and to methods of controlling odors and degrading compounds contained in wastewater in particular.

38 Claims, No Drawings

WASTE WATER TREATMENT

CROSS-REFERENCE TO RELATED APPLICATIONS

This application is a continuation of U.S. application Ser. No. 12/101,296 filed Apr. 11, 2008, now U.S. Pat. No. 7,731,851, which claims priority or the benefit under 35 U.S.C. 119 of U.S. provisional application No. 60/911,308 filed Apr. 12, 2007, the contents of which are fully incorporated herein by reference.

CROSS-REFERENCE TO DEPOSITED MATERIALS

The present application refers to deposited microorganisms. The contents of the deposited microorganisms are fully incorporated herein by reference.

BACKGROUND OF THE INVENTION

1. Field of the Invention

The present invention relates to wastewater treatment in general and to methods of controlling odors, reducing chemical oxygen demand (COD), and degrading compounds contained in wastewater in particular.

2. Description of Related Art

The main chemical compounds in wastewater are nitrogen, phosphorus, fats, oils and grease.

Objectionable odors are caused by a variety of substances typically present in wastewater. These include sulfur and several sulfur containing compounds including hydro sulfuric acid, sulfuric acid, mercaptans (R-SH) including especially methyl and dimethyl mercaptans, and dimethyl disulfide (DMDS); numerous organic acids including propionic acid, acetic acid, butyric acid, isovaleric acid; ammonia; urea; and various terpenes including carene, pinene, limonene. These substances most frequently lead to noticeable odors under anaerobic conditions.

Octel Gamlen has sold a wastewater treatment composition comprising a strain of each of *Mucor hiemalis, Trichoderma atroviride, Paecilomyces variottii*, and *Aspergillus niger.*

U.S. Pat. No. 7,160,458 discloses a method for purifying process water from a kerosene desulfurization plant comprising adding bacterial species.

It is an object of the invention to provide an improved wastewater treatment composition.

SUMMARY OF THE INVENTION

The present invention is directed to wastewater treatment compositions comprising a strain of *Mucor racemosus, Paecilomyces lilacinus, Aspergillus ustus* or *Trichoderma inhamatum* (anamorph is *Hypocrea gelatinosa*).

In another embodiment, the present invention relates to methods for the treatment of wastewater comprising adding to the wastewater a strain of *Mucor racemosus, Paecilomyces lilacinus, Aspergillus ustus* or *Trichoderma inhamatum* (anamorph is *Hypocrea gelatinosa*).

The present invention also relates to a process of degrading compounds contained in a wastewater and biologically pure cultures of one or more microbial strains.

DETAILED DESCRIPTION OF THE INVENTION

Wastewater Treatment Compositions

The present invention is directed to wastewater treatment compositions comprising a strain of *Mucor racemosus, Paecilomyces lilacinus, Aspergillus ustus* or *Trichoderma inhamatum* and to methods for the treatment of wastewater comprising adding to the wastewater a strain of *Mucor racemosus, Paecilomyces lilacinus, Aspergillus ustus* or *Trichoderma inhamatum*.

Strains of *Mucor racemosus, Paecilomyces lilacinus, Aspergillus ustus* and *Trichoderma inhamatum* strains were deposited for patent purposes under the terms of the Budapest Treaty at the NRRL USDA-ARS Patent Culture Collection, 1815 N. University Street, Peoria, Ill. 61604. The deposits were made on Mar. 20, 2007 by Novozymes Biologicals Inc. and were accorded deposit numbers:

| | |
|---|---|
| *Mucor racemosus* | NRRL 50031 |
| *Paecilomyces lilacinus* | NRRL 50032 |
| *Aspergillus ustus* | NRRL 50033 |
| *Trichoderma inhamatum* | NRRL 50034 |

In a preferred embodiment, the wastewater composition comprises a strain of *Mucor racemosus*.

In another preferred embodiment, the wastewater composition comprises a strain of *Paecilomyces lilacinus*.

In another preferred embodiment, the wastewater composition comprises a strain of *Aspergillus ustus*.

In another preferred embodiment, the wastewater composition comprises a strain of *Trichoderma inhamatum*.

In another preferred embodiment, the wastewater composition comprises a strain of *Mucor racemosus* and *Paecilomyces lilacinus*.

In another preferred embodiment, the wastewater composition comprises a strain of *Mucor racemosus* and *Aspergillus ustus*.

In another preferred embodiment, the wastewater composition comprises a strain of *Mucor racemosus* and *Trichoderma inhamatum*.

In another preferred embodiment, the wastewater composition comprises a strain of *Paecilomyces lilacinus* and *Aspergillus ustus*.

In another preferred embodiment, the wastewater composition comprises a strain of *Paecilomyces lilacinus* and *Trichoderma inhamatum*.

In another preferred embodiment, the wastewater composition comprises a strain of *Aspergillus ustus* and *Trichoderma inhamatum*.

In another preferred embodiment, the wastewater composition comprises a strain of *Mucor racemosus, Paecilomyces lilacinus*, and *Aspergillus ustus*.

In another preferred embodiment, the wastewater composition comprises a strain of *Mucor racemosus, Paecilomyces lilacinus*, and *Trichoderma inhamatum*.

In another preferred embodiment, the wastewater composition comprises a strain of *Paecilomyces lilacinus, Aspergillus ustus* and *Trichoderma inhamatum*.

In another preferred embodiment, the wastewater composition comprises a strain of *Mucor racemosus, Paecilomyces lilacinus, Aspergillus ustus* and *Trichoderma inhamatum*.

The strains may be wild-type or mutant strains.

In a preferred embodiment, the composition comprises the microorganism at a concentration of $1 \times 10^2$ to $1 \times 10^9$ colony forming units (CFU)/mL, preferably $1 \times 10^4$ to $1 \times 10^9$ colony forming units (CFU)/mL. When the composition contains more than one microorganism, each microorganism is present at a concentration of $1 \times 10^4$ to $0.5 \times 10^9$ colony forming units (CFU)/mL.

In another preferred embodiment, the composition further comprises nutrients for the microorganism(s). For example, the nutrients may be an inorganic phosphorus compound, particularly a soluble phosphate or an ortho phosphate, preferably, phosphoric acid, mono, di, or tri sodium phosphate, or diammonium phosphate. In addition, the nutrients may be ammonia ($NH_3$) or an ammonium ($NH_4^+$) salt, preferably anhydrous ammonia, ammonia-water solutions, ammonium nitrate, or diammonium phosphate. The nutrients may also be trace metals, preferably aluminum, antimony, barium, boron, calcium, cobalt, copper, iron, lead, magnesium, manganese, molybdenum, nickel, strontium, titanium, tin, zinc, and/or zirconium.

In another preferred embodiment, the composition further comprises a sugar selected from the group consisting of arabinan, arabinose, cellulose, fructose, galactan, galactose, glucan, glucose, mannan, mannose, sucrose, xylan, and xylose, or wood fiber, wood pulp, or other pulping byproducts. Preferably, the composition comprises the sugar at a concentration between 100 and 400 mg/L, when the sugar is a monosaccharide and a concentration between 8,000 and 15,000 mg/L, when the sugar is a polysaccharide.

The wastewater to be subjected to the process of this invention may contain sufficient nutrients, e.g., nitrogen and phosphorus, for culturing without the need for any additional source of nitrogen or phosphorus being added. However, in the event the wastewater is deficient in these components, nutrients can be added to the wastewater. For example, phosphorous can be supplemented, if necessary, by addition of a phosphorous source such an inorganic phosphorus compound, particularly a soluble phosphate or an orthophosphate, preferably, phosphoric acid, mono, di, or tri sodium phosphate, or diammonium phosphate, to achieve a phosphorus level in the wastewater of about 1 ppm or more per 100 $BOD_5$. Similarly, a nitrogen source, such as ammonia ($NH_3$), urea, or an ammonium salt, preferably anhydrous ammonia, ammonia-water solutions, ammonium nitrate, or diammonium phosphate, can be added to achieve an available nitrogen content of at least about 10 ppm or more per 100 $BOD_5$.

In another embodiment, the nutrients comprise trace metals, preferably aluminum, antimony, barium, boron, calcium, cobalt, copper, iron, lead, magnesium, manganese, molybdenum, tin, or zinc.

Methods for Treating Wastewater

The present invention also relates to methods for treating wastewater with a wastewater treatment composition of the present invention.

The wastewater treatment process of the present invention may reduce odor, as well as degrade compounds contained in wastewater such as butanoic acid, 2-methylphenol, heptanoic acid, nonanoic acid, 5-bromothiophene-2-carboxamide, isoxazolidine and 2-methyl-1-nitropropane.

Other odor-causing compounds which may be degraded by a wastewater treatment composition of the present invention are hydrogen sulfide, trimethylamine, methanethiol, butanoic acid, 3-methylbutanoic acid, pentanoic acid, 4-methylphenol, dimethylsulfide, dimethyldisulfide, propanoic acid, acetic acid, 2-methylpropanoic acid, indole, and 3-methyl-1H-indole.

The wastewater treatment compounds may also reduce chemical oxygen demand (COD) of wastewater.

The strains used in the present invention can be cultured in wastewater from, e.g., a pulp or paper mill either using a batch process, a semi-continuous process or a continuous process, and such is cultured for a time sufficient to degrade compounds present in the wastewater and remove them or break them down into components capable of being degraded by other organisms normally found in biological wastewater treatment systems.

The microbial strains of this invention can be employed in ion exchange resin treatment systems, in trickling filter systems, in carbon adsorption systems, in activated sludge treatment systems, in outdoor lagoons or pools, etc.

Basically, all that is necessary is for the microorganism(s) to be placed in a situation of contact with the wastewater effluent from a pulp or paper mill. In order to degrade the material present in the wastewater, the wastewater is treated with the organism(s) at a temperature between 15° C. and 45° C., preferably between 20° C. and 45° C., more preferably between 18° C. and 37° C., and most preferably between 30° C. and 35° C. Desirably, the pH is maintained in a range of 4 and 10, preferably 4.5 to 8.5. The pH can be controlled by monitoring of system and an addition of appropriate pH adjusting materials to achieve this pH range.

In general, the treatment is conducted for a sufficient time to achieve the reduction in odor or degradation of compounds desired and, in general, about 24 hours to about 8 weeks or longer, although this will depend upon the temperature of culturing, the liquor concentration and volume to be treated and other factors. In a preferred embodiment, the wastewater is treated with the microorganism(s) for between 2 hours and 14 days, preferably between 2 hours and 5 days.

The treatment can be conducted under aerobic or anaerobic conditions. When aerobic conditions are used, the treatment is conducted at a dissolved oxygen concentration of between 0.5 and 7.0 milligrams per liter. These conditions can be simply achieved in any manner conventional in the art and appropriate to the treatment system design being employed. For example, air can be bubbled into the system, the system can be agitated, a trickling system can be employed, etc. In an aerobic process, the treatment is done at a REDOX potential between −200 mV and 200 mV, preferably between 0 mV and 200 mV. When anaerobic conditions are used, the treatment is done at a REDOX potential between −550 mV and −200 mV.

Normally aerobic measures are undertaken to reduce colorants and biochemical oxygen demand (BOD) in wastewater. Aerobic technologies include trickling filter, activated sludge, rotating biological contactors, oxidation ditch, sequencing batch reactor and even controlled wetlands.

An anaerobic or anaerobic-friendly type of technology can also be used for treating the wastewater. Anaerobic technologies currently available are high-rate systems including continuous-flow stirred tank reactors, contact reactors, upflow sludge blankets, anaerobic filters (upflow and downflow), expanded or fluidized bed and two-stage systems that separate the acid-forming and the methane-forming phases of the anaerobic process.

Aerobic and anaerobic processes can be combined into a treatment system. Anaerobic treatment may be used for removing organic matter in high concentration streams, and aerobic treatment may be used on lower concentration streams or as a polishing step to further remove residual organic matter and nutrients from wastewater.

In a preferred embodiment, the wastewater treatment comprises 1-5 cycles, preferably 1 cycle or two cycles, of treatment with the microorganism(s). Preferably, each cycle comprises alternating aerobic and anaerobic treatments. More preferably, the first cycle is conducted under aerobic conditions. In a preferred embodiment, the cycles are conducted in a sequencing batch reactor. In another preferred embodiment, the process further comprises adding an alkali between cycles.

Preferably, the wastewater is a pulp and paper mill wastewater such as strong or concentrated pulp mill wastewater, weak black liquor, acid stage bleach plant filtrate, or alkaline stage bleach plant filtrate. Other types of wastewaters that might be treated include cleaning and laundry wastewaters, food processing wastewaters, and industrial process waters such as vegetable oil extractions or waste materials having fiber-containing by-products.

The process also can be used to treat waste from chemical color separation processes commonly used in wastewater treatment, including gravity clarifiers, gas flotation units, or in filtration processes such as membrane processes.

In another preferred embodiment, the ratio of solids to liquid waste is between 1:50 to 10:1 preferably 1:10 to 5:1.

In another preferred embodiment, the wastewater passes through wood fibers at anaerobic conditions, particularly in a packed biological reactor or column, an artificial wetland, or an anaerobic sequencing batch reactor (AnSR). Alternatively, the wastewater passes through a mass comprising waste wood fiber from a pulp & paper process, lime, and fly ash. Preferably, the wastewater passes through wood fiber together with cellulosic fiber, plastic, powdered or ceramic media. The rate of the wastewater is preferably 0.05-1 liter wastewater/day per kilogram of wet wood fiber mass.

In a most preferred embodiment, wood fiber is used as a biological medium at anaerobic conditions, comprising one or more of the following steps of: (a) sequencing batch reactors, (b) a facultative lagoon or a stabilization basin, (c) an activated sludge system, (d) coagulation and flocculation followed by settling, and (e) filtration.

The wastewater may be treated with the microorganism(s) in the presence of an electron acceptor, particularly chloroethanes, chloroform, chlorolignins, chloromethanes, chlorophenols, humates, lignin, quinines, or sulfonated lignins.

The microorganisms of the present invention can be employed alone or in combination with conventionally means for treating wastewater, e.g., chemical (e.g., alum, ferric, lime or polyelectrolytes), biological (e.g., white rot fungus), and physical processes (e.g., ultrafiltration, ion exchange and carbon absorption).

In the above manner, organic compounds which are present in such wastewater streams, can be advantageously treated to provide treated wastewater suitable for discharge after any additional conventional processing such as settling, chlorination, etc. into rivers and streams.

Formulations

The individual fungal strains or the blends noted above can be provided on the original media material used to culture the strains, or they can be removed from the original growth substrate by various physical mechanisms and reblended on a separate substrate or addition to achieve the desired concentration for a given application. For example, fungal spores or other discreet propagules might be removed by sonication, washing, or substrate breakdown, followed by a concentration strep such as sieving, centrifugation, or other size-exclusion techniques familiar to those skilled in the art. Such separated and/or concentrated, propagules may be either blended and applied directly, or placed on a separate substrate for application. In this way, undesirable physical properties of the original growth substrate, such as lack of solubility, or poor liquid pumping characteristics, can be improved and the product may be more readily, easily, or economically applied. In a preferred embodiment, fungal spores of the *Mucor racemosus* strain can be removed from the growth media by sonication, concentrated by sieving and centrifugation, then combined with one or more of the other strains, to provide a liquid concentrate suspension that may be automatically delivered by pumping to the desired wastewater reaction area. Various suspension agents and/or surfactants could be added to aid pumping or reduce settling of the concentrated fungal propagule blend.

Cultures

The present invention also relates to a biologically pure culture of a strain of *Mucor racemosus, Paecilomyces lilacinus, Aspergillus ustus* or *Trichoderma inhamatum*.

The following examples are given as exemplary of the invention but without intending to limit the same. Unless otherwise indicated herein, all parts, percents, ratios and the like are by weight.

EXAMPLES

Example 1

Materials and Methods

Media and Substrates:
Pulp and Paper Mill waste streams: The wastewater used in the laboratory studies were obtained from various pulp and paper mills in the U.S. and France. The waste stream material was brought to pH 7.8 by the addition of a nutrient (N&P) amended media based on SSC (see the table below).

| SAMPLE A | SAMPLE B |
|---|---|
| packaged in 0.5 kg water-soluble sachet | packaged boxes of bulk powder |
| 2 fungal strains: | 3 fungal strains: |
| Mucor hiemalis | Mucor hiemalis |
| Trichoderma atroviride | Aspergillus niger |
|  | Paecilomyces variottii |
| Carrier of fungi: maltodextrine | Carrier of fungi: maltodextrine |
| Additional medium (excipient): lithothamne | Additional medium (excipient): wheat bran |
| Dosage rate: 2 g of A per kg of COD | Dosage rate: 2 g of B per kg of COD |
| Total count: $1 \times 10^4$ propagules per gram | Total count: $1 \times 10^4$ propagules per gram |

Industrial Waste Stream: The waste stream was used as received in this study except where noted. The waste stream comes from a site that produces architectural and functional coatings and plastics additives (impact modifiers and processing aids) and has regular problems with latex. The pH of the waste stream was found to be 8.9 and it was also found to contain a number of protozoa. The soluble COD was 477+/−8 mg/L. The waste stream was reported to have an average influent COD of 1400 mg/L with an effluent COD of 400 mg/L. The waste stream as received had a low COD which was not due to COD loss during transportation, but instead was due to the low COD of the waste stream when collected. Microscopic examination of the waste revealed protozoa present in the sample.

Laundry Waste Stream: The laundry waste stream was used as received and was from a denim fabric factory with 0.2% Aquazyme Ultras 1200 L. The initial pH of this waste stream was 5.6.

Waste stream preparation: Sterilization of the waste stream where noted was accomplished by filtration. The waste stream was first centrifuged at 12,000×G for 60 minutes. This material was then passed in 100-150 mL aliquots over Whatman 934-AH filters, followed by filtration through Whatman GF/F filters, followed by filtration though a Gelman Sciences 0.45 micro-m Metricel membrane filter. Final sterilization was accomplished by filtering though a pre-sterilized Nalgene filtration unit equipped with a 0.22 micro-m membrane filter.

Nutrient Additions: The components of the nutrient media are listed in the table below. These were prepared as a ten fold concentrate and added to the waste stream to give the final concentrations listed in the following table.

| Nutrient Media | |
|---|---|
| Component | (g/L) |
| $K_2HPO_4$ | 2.0 |
| $KH_2PO_4$ | 3.06 |
| $NH_4Cl$ | 0.8 |
| $MgSO_4 \cdot 7H_2O$ | 0.2 |
| $CaCl_2 \cdot H_2O$ | 0.01 |
| $ZnSO_4$ | 0.000140 |
| $MnSO_4 \cdot H_2O$ | 0.000084 |
| $NaMoO_4 \cdot 2H_2O$ | 0.000024 |
| $FeSO_4 \cdot 7H_2O$ | 0.000028 |
| $CuSO_4 \cdot 5H_2O$ | 0.000025 |
| $CoCl_2 \cdot 6H_2O$ | 0.000024 |

Adjust pH to 7.5 with KOH

Culture Conditions: Incubations of the pulp mill waste were carried out in sterile 150 mL serum vials containing 10 mL of filter-sterilized waste. The tops of the vials were covered with "steam paper" to allow for oxygen transfer. Incubations were carried out at 30° C. The reactions with the Laundry waste and the Industrial waste were carried out in 250 mL shake flask with 50 or 100 mL of filter-sterilized waste.

Inoculum Preparation: For experiments involving the formulated Sample A, Sample B, or NZB-C sample product, to 0.1-1 grams of product was added sterile phosphate buffer to give a final concentration of 0.11 grams product/ml of buffer. This was then agitated on a wrist action shaker for 30 minutes. Except were noted, the products were added to a final concentration of 1 gram/300 mL waste stream.

Dry product production: The dry products used in this study had the characteristics listed in table below. The sample products were made by first growing the isolated fungus in 110 gram lots on a medium consisting of 50 grams of rice hulls, 50 grams bran and 10 grams starch. To this material was added 100 mL of 50% potato dextrose agar (PDA) for moisture. The material was autoclaved and inoculated with fungal mycelia and spores from pre-grown PDA plates. With the exception of *P. chrysosporium*, all incubations were initially carried out at 25° C. for 7-10 days in a humidified growth chamber in 190×100 mm glass dishes. *P. chrysosporium* was initially cultured at 39° C. At the end of the initial incubation, the cultures were removed from the humidified growth chamber and allow to air dry at room temperature for an additional 5-7 days. Final drying was accomplished under reduced pressure in a lyophilizer.

The raw material was then subjected to hydration and serial dilution to determine the number of propagules/gram using standard laboratory procedures. With the exception of *P. chrysosporium*, all fungi had yields of $1.0 \times 10^9$ to $1.0 \times 10^7$ propagules/gram. *P. chrysoporium* yielded $4.0 \times 10^3$ propagules/gram.

| Concentration (propagules/gram) of Organisms in NZB-C Dry Formulated sample | |
|---|---|
| SINGLE ORGANISMS | NZB-C |
| *Mucor racemosus* | $2.0 \times 10^5$ (range 0.1 to $10 \times 10^5$) |
| *Aspergillus ustus* | $2.9 \times 10^5$ (range 0.1 to $10 \times 10^5$) |
| *Paecilomyces lilacinus* | $1.3 \times 10^5$ (range 0.1 to $10 \times 10^5$) |
| *Trichoderma inhamatum* | $3.0 \times 10^5$ (range 0.1 to $10 \times 10^5$) |
| Total | $9.2 \times 10^5$ (range 0.4 to $40 \times 10^5$) |

COD Assay: At the indicated time, soluble COD was determined by Method 5220C (Standard Methods). All material was centrifuged at 13,000×G for 20 minutes to remove particulates. All data represents soluble COD and unless noted the mean of three determinations +/− one standard deviation unit.

Results:

Experiments with Pure Cultures: In order to assess the role of individual fungi, pure and mixed cultures of the fungi were incubated with waste from a pulp and paper mill "strong pond." The species and concentration of each fungus are listed in the table below. It is important to note that for the fungal consortia, the competitor fungi were added in greater concentrations.

| ORGANISMS AND THEIR CONCENTRATIONS USED FOR "PURE" CULTURE STUDIES | | | | |
|---|---|---|---|---|
| Single Organisms | Propagule/mL | Consortia Name | Consortia Composition | Propagule/mL |
| *Mucor racemosus* | $1.8 \times 10^4$ | Sample A | | |
| *Hypocrea gelatinosa* | $2.8 \times 10^5$ | | *Trichoderma atroviride* | $1.4 \times 10^5$ |
| *Phenerochaete chrysosporium* | $1.0 \times 10^4$ | | *Mucor hiemalis* | $1.8 \times 10^7$ |
| *Aspergillus ustus* | $3.2 \times 10^4$ | Sample B | | |
| *Paecilomyces lilacinus* | $1.4 \times 10^5$ | | *Mucor hiemalis* | $8.0 \times 10^5$ |
| *Aspergillus* sp. | $5.4 \times 10^7$ | | *Paecilomyces variottii* | $2.7 \times 10^4$ |
| | | | *Aspergillus niger* | $3.1 \times 10^4$ |

The degradation of the waste from the primary clarifier from a pulp and paper mill is shown in Table 1. The NZB-C sample demonstrated better removal of COD than the competitor samples.

TABLE 1

Laboratory pulp and paper mill wastewater assessment; 9 Days post-treatment

| Treatment | Total COD (mg/L) | % COD Reduction vs. Control |
|---|---|---|
| Control | 310 | 0 |
| Sample A | 285 | 5 |
| Sample B | 270 | 13 |
| NZB-C | 225 | 28 |

Example 2

For this experiment, a total of 60 150 ml serum vials were used and were capped with butylated rubber stoppers. Each sample was done in triplicate. Vials were then sterilized by autoclave @121° C. for 30 min.

The wastewater was obtained from France. Due to the large amount of particulate matter suspended in the samples, the middle and outlet wastewaters were filtered. Filtering was accomplished by using successively smaller filter sizes until the final filter size was 0.2 micro-m. A Whatman 934-AH filter (1.5 micro-m) was used first to remove large particulate matter in the samples. Then a Fisherbrand 0.45 micro-m Membrane MCE filter (catalog #09-719-2E) and Fisherbrand 0.2 micro-m Membrane MCE filter (catalog #09-719-2B) was used successively to achieve the desired filtration size.

After filter-sterilizing the middle and outlet waste, a 10 ml volume of wastewater was added to each of the vials under a laminar flow hood. Each vial was supplemented with 1×SSC to aid in fungal growth.

A 1×SSC nutrient media was prepared as follows:

| 1xSSC Nutrient Media | |
|---|---|
| Component | g/L |
| $K_2HPO_4$ | 2.0 |
| $KH_2PO_4$ | 3.06 |
| $NH_4Cl$ | 0.8 |
| $MgSO_4 \cdot 7H_2O$ | 0.2 |
| $CaCl_2 \cdot H_2O$ | 0.01 |
| $ZnSO_4$ | 0.000140 |
| $MnSO_4 \cdot H_2O$ | 0.000084 |
| $NaMoO_4 \cdot 2H_2O$ | 0.000024 |
| $FeSO_4 \cdot 7H_2O$ | 0.000028 |
| $CuSO_4 \cdot 5H_2O$ | 0.000025 |
| $CoCl_2 \cdot 6H_2O$ | 0.000024 |

Adjust pH to 7.5 with KOH

1×SSC was added to each of the serum vials. To prepare the inocula from the two dry products (NZB-C, a consortium of strains of *Mucor racemosus, Paecilomyces lilacinus, Aspergillus ustus*, and *Trichoderma inhamatum* deposited with NRRL and accorded deposit nos. NRRL 50031, NRRL 50032, NRRL 50033, and NRRL 50034, respectively, and Bi-Chem1005PP, a bacterial product from Novozymes Biologicals) 2.5 g of the product was added to 25 ml of sterile phosphate buffer in a sterile test tube which was then agitated on a wrist action shaker for 15 min. To prepare the inocula from a single fungal strain culture, a plate of each strain was obtained and the mixture of spores and mycelia were scraped from the surface of the plate with a sterile cotton swab. The swab was then submerged in 99 ml 0.3 mM phosphate buffer with 2 mM $MgCl_2$, pH 7.4 and vigorously agitated for 15 min to release the spores/mycelia into the buffer. Due to the absorbent properties of the cotton swabs, some volume of the phosphate buffer was lost. The volume was brought back to 10 ml after completion of the swabbing of the plate. In the case of *Mucor*, two plates of *Mucor* grown on PDA were cut into 8 sections and were added to 99 ml of phosphate buffer. After agitation, the inocula (dry blend or scrapped from individual culture) was set to stand for 10 min allowing the particulate matter to settle, then 100 microliters of each suspension was taken and used to inoculate the corresponding serum vials containing the wastewater and 1×SSC. Vials were then incubated at 35° C. for 14 days.

GC/MS with SPME Analysis of Treated Wastewater from Norampac

In order to detect specific compounds present in the wastewater, GC/MS (Gas chromatography/Mass spectrometry) analysis of the samples was conducted using SPME (Solid-Phase Microextraction). After COD analysis of each sample, the remainder of the sample (roughly 9 ml) was added to a 20 ml head space vial. A Divinylbenzene/Carboxen/Polydimethylsiloxane (DVB/CAR/PDMS) fiber (grey holder) was selected. The samples were heated to 60° C. for 5 minutes while being agitated at 320 rpm for 5 seconds and off for 30 seconds to aid in volatilization. Samples were then extracted for 30 minutes at 60° C. while being agitated as prescribed before. Samples were desorbed for 1 minute at 250° C. The split ratio was set to 1:2 and the septum purge was set at 2.5 ml/min. The samples were analyzed on a SPB-1 sulfur column because it was believed that sulfurous compounds contributing to the odor would be present in the samples. After desorbtion, the column was held at 40° C. for 3 minutes. Then the temperature was raised to 125° C. at a rate of 4° C./min. This was followed by a more rapid ramp of 25° C./min to 200° C. The mass spectrometer was set to scan from 45-1000 amu after a fresh tune.

GC/MS with SPME Analysis of Treated Wastewater from Norampac Trial 2

After it was confirmed that compounds can be detected using GC/MS with SPME, a second trial was set up in order to show degradative ability of the unknown compounds in the wastewater. It was hypothesized that if NZB-C was capable of degradation then it would show up in the chromatograms generated from untreated vs. treated samples. For example, a peak with a retention time of 16.382 minutes in an untreated sample should theoretically show up at 16.382 minutes in the treated sample. One could analyze the areas of these peaks and draw a conclusion as to the degradative ability of the fungal product. For this particular study, outlet water from Norampac was filtered through a 0.2 micro-m sterile filter, and then added to each respective 20 ml headspace vile. This was done in triplicate. SSC was added to each vial to bring the SSC concentration to 1×. The following recipe was used for this:

| SSC Trace Minerals Solution for 10xSSC preparation | |
|---|---|
| Component | mg/L |
| $ZnSO_4 \cdot 7H_2O$ | 140.0 |
| $MnSO_4 \cdot H_2O$ | 84.0 |
| $NaMoO_4 \cdot 2H_2O$ | 24.0 |
| $FeSO_4 \cdot 7H_2O$ | 28.0 |
| $CuSO_4 \cdot 5H_2O$ | 25.0 |
| $CoCl_2 \cdot 6H_2O$ | 24.0 |
| DI Water | To 1000 mL |

The media components for ten fold concentrate of SSC are shown in the following table. A white precipitate will form and is normal. The 10× medium is shaken then diluted 10 fold before use into distilled water. The final medium may be autoclaved, but filter sterilization is preferred.

| 10X SSC Nutrient Medium | |
|---|---|
| Component | g/L |
| $K_2HPO_4$ | 20.0 |
| $KH_2PO_4$ | 30.6 |
| $NH_4Cl$ | 8.0 |
| $MgSO_4 \cdot 7H_2O$ | 2.0 |
| $CaCl_2 \cdot H_2O$ | 0.1 |
| $FeCl_3$ | 0.05 |
| $SSC_3$ Trace Minerals Solution found in Table 2 | 10.0 mL |
| DI Water | To 1000 mL |

Adjust pH to 7.0-7.5 with KOH

To prepare the treated samples, a 10% solution of NZB-C was prepared using 2.5 g of NZB-C dry product added to 25 ml of sterile phosphate buffer housed in a 50 ml test tube. The tube was the agitated for 15 minutes. Once agitation was complete and the bran was allowed to settle to the bottom, 100 microliters were taken from the liquid layer above the bran. This was used to inoculate each of the respective treated vials. Vials were then capped and incubated at 30° C. for 14 days and then read using the GC/MS protocol prescribed in the previous section entitled, "GC/MS with SPME Analysis of Treated Wastewater from Norampac."

GC/MS with SPME Analysis of Treated Wastewater from Norampac Trial 2

After confirming that certain compounds could be detected using GC/MS headspace analysis with SPME, a comparison of the degradation of the compounds by simple peak comparison between treated and untreated samples was made. Three peaks were isolated for this comparison study. The identity of these peaks was provided by the internal compound library of the Shimadzu GC/MS system used (GCMS-QC2010S). The results are provided in Table 2. It is evident that NZB-C is able to degrade these detected compounds.

TABLE 2

Assessment of NZB-C Activity against Waste Compounds in Pulp and Paper Mill Middle and Outlet Wastewater using GC/MS with SPME.

| | Amount Remaining - Control (Peak area units) | Amount Remaining - NZB-C (Peak area units) | % NZB-C Degradation Improvement vs. Control |
|---|---|---|---|
| Compound in Middle Waste Water | | | |
| 5-bromo-thiophene-2-carboxamide | 3,058 | 1,721 | 43.7 |
| Isoxazolidine | 9,945 | 8,860 | 10.9 |
| Dodecamethylcyclohexasiloxane | 13,064 | 11,987 | 8.2 |
| Compound in Outlet Waste Water | | | |
| 5-bromo-thiophene-2-carboxamide | 6,800 | 1,822 | 73.2 |
| Isoxazolidine | 10,779 | 7,177 | 33.4 |
| 2-methyl-1-nitropropane | 4,507 | 1,228 | 72.7 |

The results show that NZB-C degrades 5-bromothiophene-2-carboxamide, isoxazolidine and 2-methyl-1-nitropropane.

Example 3

A field assessment of the ability of the NZB-C fungal consortium to reduce odor-causing and certain recalcitrant waste compounds in a Pulp and Paper mill lagoon treatment facility in Bonduelle, France was undertaken. NZB-C material, prepared as described above, was added at a rate of 1.5 g NZB-C per 1.0 Kg of total COD present into a treatment lagoon with a flow rate of 7,500 m³/day. A similar but separate lagoon on location was not treated with NZB-C and served as a control. Samples were taken at the lagoon outlet at the initiation of the experiment (Day 0) and at Day 23. These were assessed using the GC/MS with SPME analytical method described in Example 1. The results are provided in Table 3, and indicate that considerable and significant reduction in certain odor-associated compounds occurred in this time period.

TABLE 3

Field Assessment of NZB-C Activity against Odor-Associated Compounds in Pulp and Paper Mill Outlet Wastewater using GC/MS with SPME.

| Odor Associated Compounds (Outlet water) | Amount Degraded - Control (Peak area units) | Amount Degraded - NZB-C (Peak area units) | % NZB-C Degradation Improvement vs. Control |
|---|---|---|---|
| Butanoic Acid | 837,019 | 894,748 | 6.90 |
| 2-Methylphenol | 192,031 | 401,809 | 109.24 |
| Heptanoic Acid | 6,275,573 | 8,593,919 | 36.94 |
| Nonanoic Acid | 708,757 | 1,410,612 | 99.03 |

What is claimed:

1. A process for treating wastewater, comprising adding to the wastewater a wastewater treatment composition comprising a strain of *Paecilomyces lilacinus, Aspergillus ustus* or *Trichoderma inhamatum*, wherein the wastewater is a pulp and paper mill wastewater.

2. The process of claim 1, wherein the wastewater treatment composition further comprises a carbohydrate selected from the group consisting of arabinan, arabinose, cellulose, fructose, galactan, galactose, glucan, glucose, mannan, mannose, sucrose, xylan, and xylose, or wood fiber, wood pulp, or other pulping byproducts.

3. The process of claim 2, wherein the wastewater treatment composition comprises the carbohydrate at a concentration between 100 and 400 mg/L, when the carbohydrate is a monosaccharide and a concentration between 8,000 and 15,000 mg/L, when the carbohydrate is a polysaccharide.

4. The process of claim 1, wherein the treatment is performed under aerobic conditions.

5. The process of claim 1, wherein the treatment is a batch, semi-continuous or continuous treatment.

6. The process of claim 5, wherein the treatment is done in cycles in a sequencing batch reactor.

7. The process of claim 6, further comprising addition of an alkali between cycles.

8. The process of claim 1 wherein the treatment of the wastewater comprises 1-5 cycles of treatments with the wastewater treatment composition.

9. The process of claim 8, wherein each cycle comprises alternating aerobic and anaerobic treatments.

10. The process of claim 9, wherein the first treatment is anaerobic.

11. The process of claim 1, further comprising adding nutrients to the wastewater.

12. The process of claim 1, wherein the chemical oxygen demand of the wastewater is reduced.

13. A process for treating wastewater, comprising adding to the wastewater a wastewater treatment composition comprising a strain of *Paecilomyces lilacinus, Aspergillus ustus* or

*Trichoderma inhamatum*, comprising passing the wastewater through wood fibers at anaerobic conditions in a packed biological reactor or column, an artificial wetland, or an anaerobic sequencing batch reactor (AnSR).

14. The process of claim 13, wherein the wastewater treatment composition further comprises a carbohydrate selected from the group consisting of arabinan, arabinose, cellulose, fructose, galactan, galactose, glucan, glucose, mannan, mannose, sucrose, xylan, and xylose, or wood fiber, wood pulp, or other pulping byproducts.

15. The process of claim 14, wherein the wastewater treatment composition comprises the carbohydrate at a concentration between 100 and 400 mg/L, when the carbohydrate is a monosaccharide and a concentration between 8,000 and 15,000 mg/L, when the carbohydrate is a polysaccharide.

16. The process of claim 13, wherein the treatment is performed under aerobic conditions.

17. The process of claim 13, wherein the treatment is a batch, semi-continuous or continuous treatment.

18. The process of claim 17, wherein the treatment is done in cycles in a sequencing batch reactor.

19. The process of claim 18, further comprising addition of an alkali between cycles.

20. The process of claim 13 wherein the treatment of the wastewater comprises 1-5 cycles of treatments with the wastewater treatment composition.

21. The process of claim 20, wherein each cycle comprises alternating aerobic and anaerobic treatments.

22. The process of claim 21, wherein the first treatment is anaerobic.

23. The process of claim 13, further comprising adding nutrients to the wastewater.

24. The process of claim 13, wherein the chemical oxygen demand of the wastewater is reduced.

25. A process for treating wastewater, comprising adding to the wastewater a wastewater treatment composition comprising a strain of *Paecilomyces lilacinus, Aspergillus ustus* or *Trichoderma inhamatum*, comprising passing the wastewater through a mass comprising waste wood fiber from a pulp & paper process, lime, and fly ash.

26. The process of claim 25, wherein the wastewater treatment composition further comprises a carbohydrate selected from the group consisting of arabinan, arabinose, cellulose, fructose, galactan, galactose, glucan, glucose, mannan, mannose, sucrose, xylan, and xylose, or wood fiber, wood pulp, or other pulping byproducts.

27. The process of claim 26, wherein the wastewater treatment composition comprises the carbohydrate at a concentration between 100 and 400 mg/L, when the carbohydrate is a monosaccharide and a concentration between 8,000 and 15,000 mg/L, when the carbohydrate is a polysaccharide.

28. The process of claim 25, wherein the treatment is performed under aerobic conditions.

29. The process of claim 25, wherein the treatment is a batch, semi-continuous or continuous treatment.

30. The process of claim 29, wherein the treatment is done in cycles in a sequencing batch reactor.

31. The process of claim 30, further comprising addition of an alkali between cycles.

32. The process of claim 25 wherein the treatment of the wastewater comprises 1-5 cycles of treatments with the wastewater treatment composition.

33. The process of claim 32, wherein each cycle comprises alternating aerobic and anaerobic treatments.

34. The process of claim 33, wherein the first treatment is anaerobic.

35. The process of claim 25, further comprising adding nutrients to the wastewater.

36. The process of claim 25, wherein the wastewater is passed through wood fiber at a rate of 0.05-1 liter wastewater/day per kilogram of wet wood fiber mass.

37. The process of claim 25, wherein the wastewater is passed through wood fiber together with cellulosic fiber, plastic, powdered or ceramic media.

38. The process of claim 25, wherein the chemical oxygen demand of the wastewater is reduced.

* * * * *